United States Patent [19]

Schumacher et al.

[11] Patent Number: 4,861,717

[45] Date of Patent: Aug. 29, 1989

[54] MICROORGANISMS AND PLASMIDS FOR THE CONSTITUTIVE FORMATION OF CREATINAMIDINOHYDROLASE AND PROCESSES FOR THE PRODUCTION THEREOF

[75] Inventors: Günter Schumacher; Peter Buckel, both of Bernried; Klaus Beaucamp, Tutzing, all of Fed. Rep. of Germany

[73] Assignee: Boehringer Mannheim GmbH, Mannheim-Waldhof, Fed. Rep. of Germany

[21] Appl. No.: 816,565

[22] Filed: Jan. 6, 1986

[30] Foreign Application Priority Data

Jan. 4, 1985 [DE] Fed. Rep. of Germany ....... 3500184

[51] Int. Cl.⁴ ..................... C12N 15/00; C12N 1/20; C07H 15/12
[52] U.S. Cl. ................................ 435/172.3; 435/231; 435/252.33; 435/252.34; 435/320; 435/849; 435/877; 536/27; 935/14; 935/82
[58] Field of Search ..................... 435/172.3, 253, 320, 435/849, 877, 227; 935/14, 29, 72, 73; 536/27

[56] References Cited

U.S. PATENT DOCUMENTS 4,039,384 8/1977 Suzuki et al. ..................... 195/62

FOREIGN PATENT DOCUMENTS 2659878 11/1977 Fed. Rep. of Germany .

OTHER PUBLICATIONS

Parke et al., *J. of Bacteriol.*, 126:272–81, 1976.
Tsuru et al., *Agr. Biol. Chem.* 40(5): 1011–1018, (1976).
Bagdasarian et al., *Gene* 16: 237–247, (1981).

*Primary Examiner*—Elizabeth C. Weimar
*Assistant Examiner*—Thomas D. Mays
*Attorney, Agent, or Firm*—Felfe & Lynch

[57] ABSTRACT

The present invention provides a micro-organism of the species *Escherichia coli* or *Pseudomonas putida*, wherein it constitutively forms creatinamidinohydrolase.

The present invention also provides a process for the production of such a micro-organism.

15 Claims, 6 Drawing Sheets

FIG. 5.

```
  1' MetGlnMetProLysThrLeuArgIleArgAsnGlyAspLysValArgSerThrPheSer       20
  1  ATGCAAATGCCCAAGACGCTCCGCATCCGTAACGGCGACAAGGTTCGCTCCACCTTCTCC       60
        *         *         *         *         *         *
 21  AlaGlnGluTyrAlaAsnArgGlnAlaArgLeuArgAlaHisLeuAlaAlaGluAsnIle       40
 61  GCCCAGGAATACGCCAATCGCCAAGCCAGGCTGCGCGCCCACCTGGCGGCGGAGAACATC      120
        *         *         *         *         *         *
 41  AspAlaAlaIlePheThrSerTyrHisAsnIleAsnTyrTyrSerAspPheLeuTyrCys       60
121  GACGCCGCGATCTTCACCTCGTACCACAACATCAACTACTACTCCGACTTCCTCTACTGC      180
        *         *         *         *         *         *
 61  SerPheGlyArgProTyrAlaLeuValValThrHisAspAspValIleSerIleSerAla       80
181  TCCTTCGGCCGCCCCTACGCGTTGGTGGTGACCCACGACGACGTCATCAGCATCAGCGCC      240
        *         *         *         *         *         *
 81  AsnIleAspGlyGlyGlnProTrpArgArgThrValGlyThrAspAsnIleValTyrThr      100
241  AACATCGACGGCGGCCAGCCGTGGCGCCGCACCGTCGGCACCGACAACATCGTCTACACC      300
        *         *         *         *         *         *
101  AspTrpGlnArgAspAsnTyrPheAlaAlaIleGlnGlnAlaLeuProLysAlaArgArg      120
301  GACTGGCAGCGCGATAACTACTTCGCCGCCATCCAGCAGGCGTTGCCGAAGGCCCGCCGC      360
        *         *         *         *         *         *
121  IleGlyIleGluHisAspHisLeuAsnLeuGlnAsnArgAspLysLeuAlaAlaArgTyr      140
361  ATCGGCATCGAACATGACCACCTGAACCTGCAGAACCGCGACAAGCTGGCCGCGCGCTAT      420
        *         *         *         *         *         *
141  ProAspAlaGluLeuValAspValAlaAlaAlaCysMetArgMetArgMetIleLysSer      160
421  CCGGACGCCGAGCTGGTGGACGTGGCCGCCGCCTGCATGCGTATGCGCATGATCAAATCC      480
        *         *         *         . *         *         *
161  AlaGluGluHisValMetIleArgHisGlyAlaArgIleAlaAspIleGlyGlyAlaAla      180
481  GCCGAAGAGCACGTGATGATCCGCCACGGCGCGCGCATCGCCGACATCGGTGGTGCGGCG      540
        *         *         *         *         *         *
181  ValValGluAlaLeuGlyAspGlnValProGluTurGlyValAlaLeuHisAlaThrGln      200
541  GTGGTCGAAGCCCTGGGCGACCAGGTACCGGAATACGAAGTGGCGCTGCATGCCACCCAG      600
        *         *         *         *         *         *
201  AlaMetValArgAlaIleAlaAspThrPheGluAspValGluLeuMetAspThrTrpThr      220
601  GCCATGGTCCGCGCCATTGCCGATACCTTCGACGACGTGGAGCTGATGGATACCTGGACC      660
        *         *         *         *         *         *
221  TrpPheGlnSerGlyIleAsnThrAspGlyAlaHisAsnProValThrThrArgLysVal      240
661  TGGTTCCAGTCCGGCATCAACACCGACGGCGCGCACAACCCGGTGACCACCCGCAAGGTG      720
        *         *         *         *         *         *
```

FIG. 5A.

```
241  AsnLysGlyAspIleLeuSerLeuAsnCysPheProMetIleAlaGlyTyrTyrThrAla    260
721  AACAAGGGCGACATCCTCAGCCTCAACTGCTTCCCGATGATCGCCGGCTACTACACCGCG    780
        *         *         *         *         *         *

261  LeuGluArgThrLeuPheLeuAspHisCysSerAspAspHisLeuArgLeuTrpGlnVal    280
781  TTGGAGCGCACCCTGTTCCTCGACCACTGCTCGGACGACCACCTGCGTCTGTGGCAGGTC    840
        *         *         *         *         *         *

281  AsnValGluValHisGluAlaGlyLeuLysLeuIleLysProGlyAlaArgCysSerAsp    300
841  AACGTCGAGGTGCATGAAGCCGGCCTGAAGCTGATCAAGCCCGGTGCGCGTTGCAGCGAT    900
        *         *         *         *         *         *

301  IleAlaArgGluLeuAsnGluIlePheLeuLysHisAspValLeuGlnTyrArgThrPhe    320
901  ATCGCCCGCGAGCTGAACGAGATCTTCCTCAAGCACGACGTGCTGCAGTACCGCACCTTC    960
        *         *         *         *         *         *

321  GlyTyrGlyHisSerPheGlyThrLeuSerHisTyrTyrGlyArgGluAlaGlyLeuGlu   340
961  GGCTACGGCCACTCCTTCGGCACGCTCAGCCACTACTACGGCCGCGAGGCCGGGTTGGAA   1020
        *         *         *         *         *         *

341  LeuArgGluAspIleAspThrValLeuGluProGlyMetValValSerMetGluProMet   360
1021 CTGCGCGAGGACATCGACACCGTGCTGGAGCCGGGCATGGTGGTGTCGATGGAGCCGATG   1080
        *         *         *         *         *         *

361  IleMetLeuProGluGlyLeuProGlyAlaGlyGlyTyrArgGluHisAspIleLeuIle   380
1081 ATCATGCTGCCGGAAGGCCTGCCGGGCGCCGGTGGCTATCGCGAGCACGACATCCTGATC   1140
        *         *         *         *         *         *

381  ValAsnGluAsnGlyAlaGluAsnIleThrLysPheProTyrGlyProGluLysAsnIle   400
1141 GTCAACGAGAACGGTGCCGAGAACATCACCAAGTTCCCCTACGGCCCGGAGAAAAACATC   1200
        *         *         *         *         *         *

401  IleArgLys *                                                    420
1201 ATCCGCAAATGA                                                   1260
        *         *         *         *         *         *
```

MICROORGANISMS AND PLASMIDS FOR THE CONSTITUTIVE FORMATION OF CREATINAMIDINOHYDROLASE AND PROCESSES FOR THE PRODUCTION THEREOF

The present invention is concerned with microorganisms and plasmids for the constitutive formation of creatinamidinohydrolase and with processes for the production thereof.

The enzyme creatinamidinohydrolase EC 3.5.3.3 is used industrially for the determination of creatinine. Therefore, it is used, inter alia, in clinical analysis for the diagnosis of kidney diseases in which creatinine contents occur in the serum and in the urine which differ from those of the healthy organism. Admittedly, micro-organisms are known, for example Pseudomonas species, which, with induction by creatine, are able to produce creatinamidinohydrolase in an amount making working up worthwhile but the achievable yields and the costs of the isolation of the enzyme still represent a limiting factor for the industrial use of the enzyme.

Therefore, there is a need for micro-organisms which do not display these disadvantages and, in particular, constitutively form creatinamidinohydrolase, i.e. without an induction being necessary for this purpose, and thereby provide substantially better yields than the previously known creatinamidinohydrolase formers. Furthermore, it is an object of the present invention to produce, according to the methods of gene technology, a micro-organism of this kind in which the genetic information for a high synthesis capacity for the stated enzyme is present in a host micro-organism which can be readily cultured and from which the enzyme can be cost-favourably isolated.

The present invention enables these objects to be achieved.

Thus, according to the present invention, there is provided a micro-organism of the species *Escherichia coli* or *Pseudomonas putida* which is characterised in that it forms creatinamidinohydrolase constitutively.

Plasmids pBT 2a-1 NRE and pBT 306.16 and *E. coli* cell line K12 ED8654, which are described in this application, have been deposited at the Deutsche Sammlung von Mikroorganismen Gesellschaft für Biotechnologische Forschung mbH, Grisebackstrasse 8, 3400 Göttingen, Federal Republic of Germany, in accordance with the Budapest Treaty on deposit of microorganisms, and in compliance with 37 C.F.R. §1.14 and 35 U.S.C. §122. These plasmids have been accorded Accession Numbers DSM 3148P (for pBT 2a-1 NRE), DSM 3149 (for pBT 306.16), and DSM 3144 (for *E. coli* K12 ED8654).

For micro-organisms of the species *Escherichia coli*, hitherto even an inductive formation of this enzyme has not been found. In the case of Pseudomonas putida, information is admittedly present for the formation of creatinamidinohydrolase but the enzyme is only formed by induction and in very low activities.

A preferred micro-organisms of the species *Escherichia coli* according to the present invention contains the new plasmid pBT 2a-1. A micro-organism of this kind is able to apply up to 50% of its total synthetic ability for protein for the formation of creatinamidinohydrolase.

A further preferred micro-organism according to the present invention is one of the species *Escherichia coli* or *Pseudomonas putida* which contains the new plasmid pBT 306.16. Such micro-organisms are also constitutive creatinamidinohydrolase formers with very high synthesis capacity.

Thus, the present invention also provides the new plasmids pBT 2a-1, DSM 3148P and pBT 306.16, DSM 3149P. Whereas the first-mentioned plasmid provides an especially high synthesis capacity in microorganisms of the species *Escherichia coli*, the second-mentioned plasmid possesses the advantage that not only in the species *Escherichia coli* but also in the species *Pseudomonas putida*, it gives a high expression of the desired enzyme.

As already mentioned, the micro-organisms or plasmids according to the present invention can be obtained by methods of gene technology.

Thus, according to the present invention, there is provided a process for the production of microorganisms of the mentioned species which constitutively form creatinamidinohydrolase, wherein DNA from *Pseudomonas putida* is (a) limitedly digested with Eco R I and a 5.8 Kb fragment is obtained or
(b) split with Eco R I and Pvu II and a 2.2 Kb fragment is obtained, the fragment obtained according to a) or b) is cloned into a vector split with the same restriction endonuclease(s), this is transformed in an *Escherichia coli* or *Pseudomonas putida* strain appropriate for the selected vector and the clones which constitutively form creatinamidinohydrolase are isolated. (Kb here means "kilobase pair", i.e. a thousand nucleotide base pairs).

The information for the expression of the creatinamidinohydrolase is present on the 5.8 Kb fragment and its sub-fragment of 2.2 Kb which is split out in the above-mentioned way with the restriction endonuclease Eco RI alone or with Eco RI, together with Pvu II. The particular fragments are cloned, according to known gene technological methods, into a vector which has been split with the same restriction endonuclease(s) in order to provide appropriate ends. Alternatively, if not also preferably, it is also possible to split vectors appropriate for Escherichia coli or *Pseudomonas putida* with other restriction endonucleases, the points of fission of which on the special vector are so arranged that the replication ability of the vector supplemented on the point of fission with one of the above-mentioned DNA fragments from *Pseudomonas putida* and its transformability into a host strain is retained. As vector, it is preferable to use the plasmid pBR 322 and to transform this, after the introduction of one of the two *Pseudomonas putida* fragments, into an appropriate *Escherichia coli* strain. Numerous *Escherichia coli* strains are known which can be readily transformed with the plasmid pBR 322 and its derivatives. Another preferred vector is the λ-phase charon 10. pBR 322, as well as derivatives thereof, are, like λ-vectors, commercially available.

According to a preferred process, pBR 322 is split with Eco R1 and Pvu II, the 2.3 Kb fragment thereby formed is isolated and linked with the 2.2 Kb Eco R1-Pvu II fragment from *Pseudomonas putida*, with the formation of a new plasmid, designated as pBT 3-2, which is transformed into *Escherichia coli*, *Escherichia coli* K12 ED 8654 DSM 3144 thereby being obtained.

*Escherichia coli* strains transformed in the above-described way with the plasmid derivative from pBR 322 can be readily selected on the basis of their ampicillin resistance. Since they are not only ampicillin-resistant but also creatinamidinohydrolase formers, nontransformed cells cannot grow and, amongst the grown cells, those which form the desired enzyme can easily be selected according to one of the methods described hereinafter in more detail.

According to the present invention, especially good results are obtained when the pBT 322 -containing, transformed *Escherichia coli* cells are treated, at the time of the amplification of the plasmid, with nitrosoguanidine, thereafter the plasmid is isolated therefrom, again transformed in *Escherichia coli* cells, this cycle is possibly repeated and from the micro-organism clones thereby obtained with an especially marked creatinamidinohydrolase activity, there is recovered the plasmid pBT 2a-1, DSM 3158P, which is also a subject of the present invention. As already mentioned above, *Escherichia coli* cells which contain this plasmid produce up to 50% of creatinamidinohydrolase, referred to their total protein formation.

A screening system which enables formed microorganism clones with an especially high activity of creatinamidinohydrolase to be identified is obtained by contacting such clones with agarose plates which contain dissolved creatine, sarcosine oxidase, peroxidase and a hydrogen peroxide colour indicator system. Those clones are then selected for the multiplication which give the strongest coloration corresponding to the strongest enzyme formation. As hydrogen peroxide colour indicator system, there is preferably used 4-aminoantipyrine in combination with an N-ethyl-N-(sulphoethyl)-3-methylaniline salt, the potassium salt being preferred.

With the process according to the present invention, there can also be produced plasmids which can be used not only for the expression of the enzyme in *Escherichia coli* but also in *Pseudomonas putida*. For this purpose, it is preferably to proceed in such a manner that, from pBT 2a-1, by splitting with the restriction endonucleases Pvu I and Pvu II, there is obtained a 2.8 Kb fragment and this is ligated with a further 10 Kb fragment which is obtained from pBT 306.1 by splitting with Pvu I and ma I. There is thus obtained the plasmid pBT 306.16, DSM 3149P, which brings about the constitutive creatinamidinohydrolase formation not only in *Escherichia coli* but also in *Pseudomonas putida*.

It is surprising that, according to the present invention, a substantial increase of the enzyme formation is achieved because it has already been reported many times that by the use of the methods of DNA new combination by increase of the copy number of a particularly gene, an increased gene expression is achieved. However, it does not follow from this that the transfer of gene from Pseudomonas in *Escherichia coli* leads, in all probability, to an increase of the gene expression. Indeed, for the majority of the genes transferred by DNA new combination from Pseudomonas into *Escherichia coli*, even a reduction of the gene expression has been reported (cf., for example, Stanisisch and Ortiz, J. Gen. Microbiol., 94, 281–289/1986; Nakazawa et al., J. Bacteriol., 134, 270–277/1978; Ribbons et al., Soc. gen. Microbiol. Quart., 6, 25–25/1978; and Franklin et al., in Microbiol. Degradation of Xenobiotics and Recalcitrant Compounds, Leisinger Cook, Hütter and Neusch ed., 1981, pp. 109–130). That such an improvement cannot be expected is shown by a consideration of the various biological synthesis steps which must take place until finally an enzymatically-active protein is formed.

The information for a protein is contained in the desoxyribonucleic acid (DNA). This DNA is converted by a DNA-dependent RNA polymerase into nRNA (ribonucleic acid messengers). The so synthesised mRNA is reacted on ribosomes to protein, three nucleotides (tripley or condon) - according to the laws of the genetic code - thereby each determining the incorporation of a particular amino acid.

Control regions in the DNA determine at which point a strand of the DNA is transcribed into mRNA (promotor sequences) or at which point the synthesis of the mRNA is stopped (termination sequence).

Stop and start sequences are also known on the level of the protein synthesis (translation). An ATG (which is translated into f-methionine) thereby, in general, determines the beginning of the protein and, for example, a TAA or a TAG the end of the translation.

The extent of the expression of a polypeptide sequence is dependent upon several factors, for example, inter alia, upon the quality of the promotor sequence, mRNA stability, secondary and tertiary structure of the mRNA, quality of the ribosomal binding site, distance of the ribosomal binding site from the start condon (ATG), nucleotide sequence between ribosomal binding site and start condon (ATG) and the presence of efficient stop signals on the transcription and translation levels. Without precise knowledge of the primary structure of the gene and of the protein coded by this, it is not possible objectively to intervene in the above-described regulation processes of the gene expression. Since this precise knowledge was not present in the present case, the improved synthesis capacity of the micro-organisms and plasmids according to the present invention could not be foreseen.

In the scope of the present invention, as *Escherichia coli* there are preferably used derivatives of the *Escherichia coli* K12 strain. Amongst these were, for example, successfully used:

*Escherichia coli* K12,
W 3350 (thi, galK, GalT, rpsl, of P. Tiollais), DSM 3141
*Escherichia coli* K12,
ED 8654 (trp R, hsd M+, hsd R−, sup E, sup F of K. Murray), DSM 2102
*Escherichia coli* K12,
CSH 1 (thi, trp, lac z, rpsl from Cold Spring Harbor strain collection), DSM 3142.

As host cells of the *Pseudomonas putida* strain, there can be used not only wild type isolates but also laboratory strains. Especially good results have been achieved with *Pseudomonas putida* 2440, DSM 2106 (Gene 1981, 237–247).

As vector systems for the expression into *Escherichia coli*, there are, according to the present invention, as mentioned, preferably used genetically manipulated derivatives of the commercially available plasmid pBR 322 (Gene, 1977, 95–113). For the expression into Pseudomonas strains, there are preferably used genetically transformed derivatives of the plasmid pRSF 1010 (Gene, 1981, 237–247). In the case of the use of the above-mentioned restriction endonucleases for the construction of the genetically transformed plasmids of the present invention, there is obtained the creatinamidinohydrolase gene section which still contains the expression-vector system and a regulation origin, which brings about an increased copy number of the vector system in the host cells, as well as gene which can easily be selected, for example by antibiotic resistance, on the basis of their products.

In the following the present invention is described in more detail with reference to the accompanying drawings and the the Examples.

Figure 3:
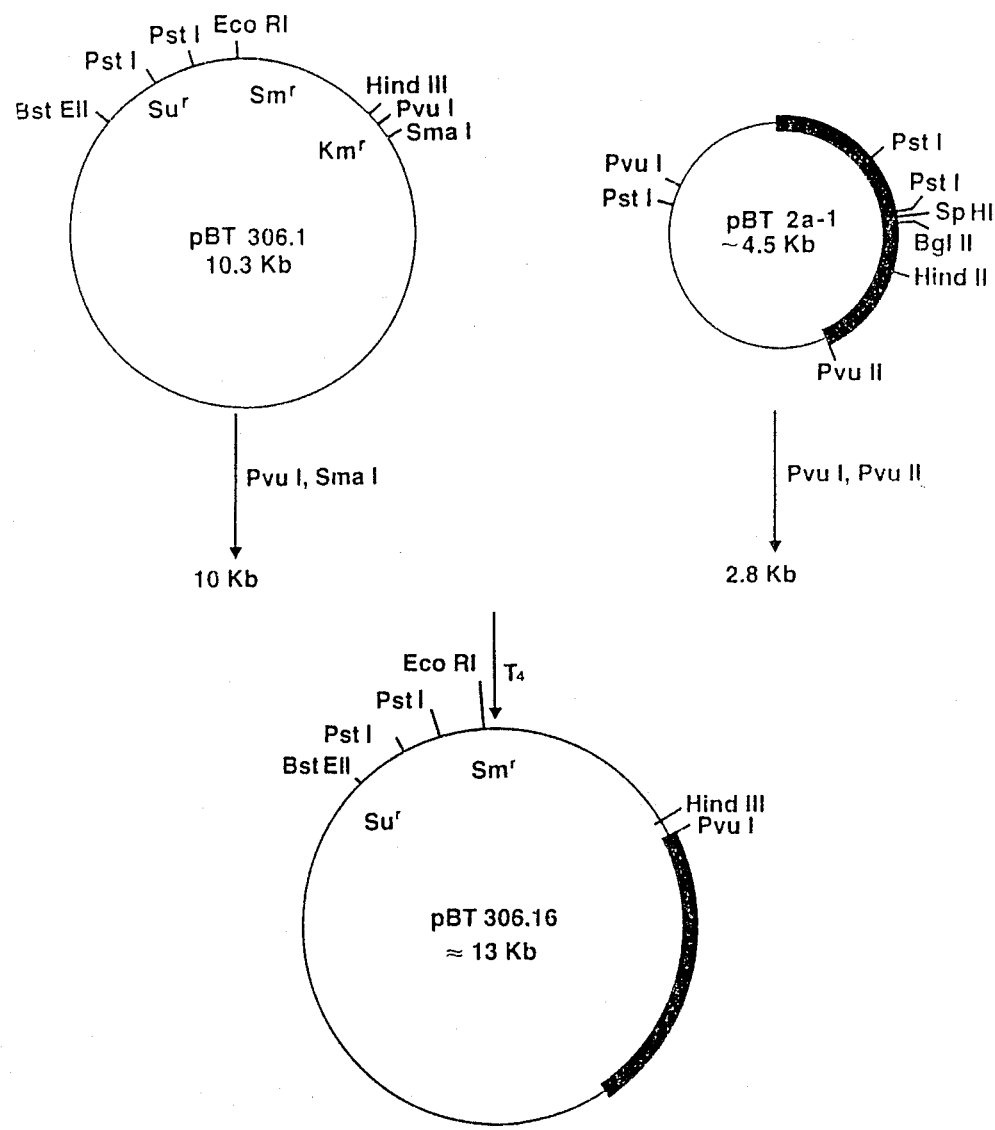
Figure 4:
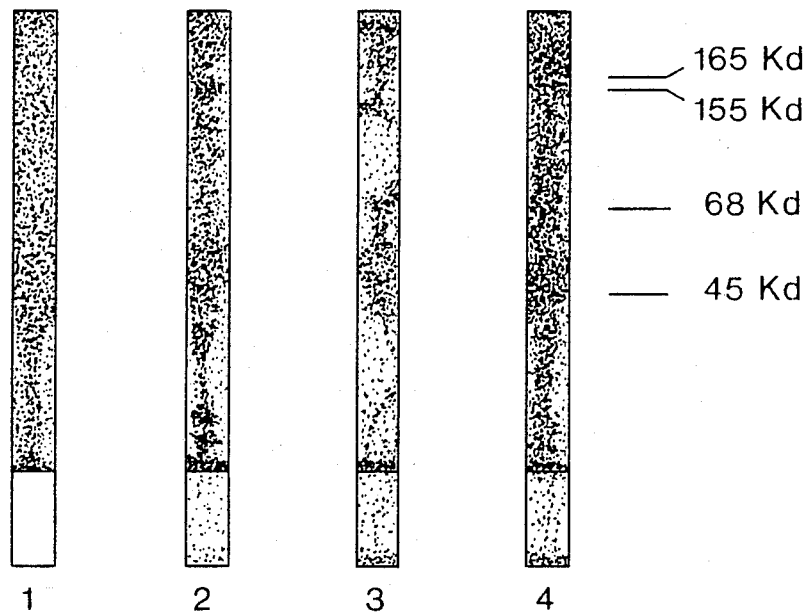

FIG. 3 schematically shows the formation of the plasmid pBT 306.16 according to the present invention from pBT 306.1 and pBT 2a-1; and FIG. 4 shows an SDS gel in which cell extracts are applied:
- column 1: starting strain *Pseudomonas putida*,
- column 2: the *Escherichia coli* host strain ED carrying the plasmid pBT 2a-1,
- column 4: host strain ED and
- column 3: for comparison, 15 μg. of the purified creatinase.

FIG. 5 shows the DNA sequence coding the enzyme creatinamidinohydrolase and the protein sequence resulting from the DNA sequence.

In order to seek out positive clones, i.e. microorganism clones which constitutively form creatinamidinohydrolase, there can, according to the present invention, be used as screening system which works according to the principle of the enzyme immuno test. Specific antibodies against the creatinamidinohydrolase are hereby fixed on to an appropriate carrier, for example a polyvinyl film and the film is placed on lysed colonies or also on plaques. After washing with water, the film is incubated with the same specific antibody in the form of an enzyme conjugate, for example with peroxidase. If an enzyme-producing clone is present, then a sandwich results of antibody-antigen and enzyme-labelled antibody. In an appropriate colour indicator system, the antibody-peroxidase conjugate gives a colour, for example in an indicator system of tetramethylbenzidine, dioctyl sodium sulphosuccinate and hydrogen peroxide in gelatine, green coloured spots are observed. This system gives a detection limit of from 10 pg. to 100 pg. of protein antigen. The preparation of such an enzyme immuno test and the preparation of appropriate antibodies can be carried out according to the introduction to "Testkombination Genexpression", Boehringer Mannhein GmbH.

The following Examples further explain the present invention:

EXAMPLE 1

(A) Isolation of the chromosomal *Pseudomonas putida* DNA.

The chromosomal DNA from *Pseudomonas putida* DSM 2106 is isolated after lysis of the cells and winding up of the DNA on a glass rod and, after 2 phenolisations and ethanol precipitation, dissolved in a concentration of 600 μg./ml. (Cosloy and Oishi, Molec. Gen. Genet., 124, 1–10/1973).

10 μg. of chromosomal DNA are partially digested using 5 units of Eco RI, E.C. 3.1.23.11, for 30 minutes and the extent of the digestion is analysed in agarose gel.

(B) Isolation and purification of λ charon 10 DNA.

$10^{10}$ Bacteria of the strain *Escherichia coli* ED DSM 2102 are incubated with $5 \times 10^8$ λ phages charon for 10 to 20 minutes at 37° C. and subsequently, up to the beginning of the lysis of the bacteria, allowed to grow in 500 ml. of whole medium. The procedure of the phage and DNA isolation takes place exactly according to the instructions of Maniatis et al., in: Moleculars Cloning, Cold Spring harbor Laboratory, 1982, 76–85.

10 μg. Charon 10 DNA are completely split with Eco RI. 1 μg. limited with Eco RI-digested chromosomal *Pseudomonas putida* DNA according to (A) is incubated with 3 μg. charon 10 DNAm split with Eco RI, with 40 units of the enzyme T4 DNA ligase. The packing of the ligated-together DNA fragments in the head and tail proteins of the phage λ takes place in a test tube. The preparation of the proteins necessary for the packing, as well as the packing of the DNA, takes place according to Maniatis et al., Molecular Cloning, Cold Spring Harbor Laboratory, 1982, 256–291 (in vitro packing systems for λ DNA particles are commercially available, for example Boehringer Mannhein GmbH "DNA packaging kit"). About 0.5 μg of the linked-together λ and *Pseudomonas putida* DNA are incubated with 20 μl of the in vitro packing batch an, after 60 minutes, there is added 0.5 ml. SM buffer (Maniatis et al., Cold Spring Harbor Laboratory, 1972, 443) and 1/200 volume (2.5 μl.) of the packing batch is incubated for 10 minutes at 37° C. with 200 μl. of an overnight culture of the strain ED, in $10^{-2}$M magnesium sulphate. The bacteria suspension is subsequently mixed with 3 ml. LB (Miller in Experiments in Molecular Genetics, Cold Spring Harbor Laboratory, 1972, 433) agarose (0.8%) and poured on to LB plates. About $10^5$ phage holes (plaques) are obtained per 1 μg. of DNA used.

For the identification of phages which contain a creatinase-coding gene, the above mentioned immunoassay is used. The indicator system consists of 6 mg./ml. tetramethylbenzidine, 20 mg./ml. dioctyl sodium sulphosuccinate and 0.01% hydrogen peroxide in 6% gelatine. Two positive plaques are identified per 1000.(C) Recloning of the creatinase gene into *Escherichia coli*.

Figure 1:
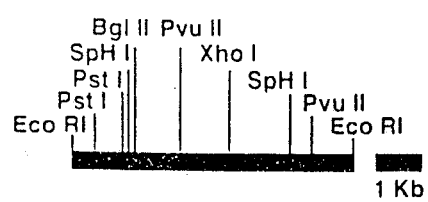
FIG. 1 is a schematic illustration of the production of the plasmid pBT 3-2 with use of the 2.2 Kb fragment from the *Pseudomonas putida* DNA and of the plasmid pBR 322 as starting material.
Figure 1:
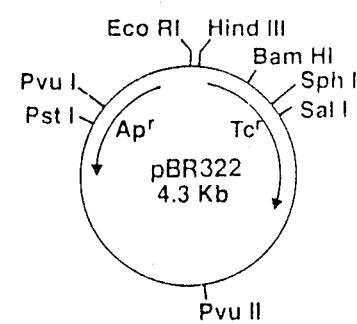
Figure 1:
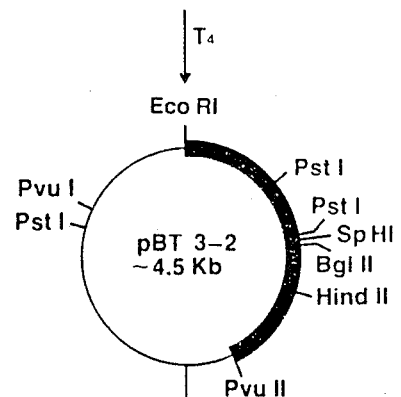
Figure 1:
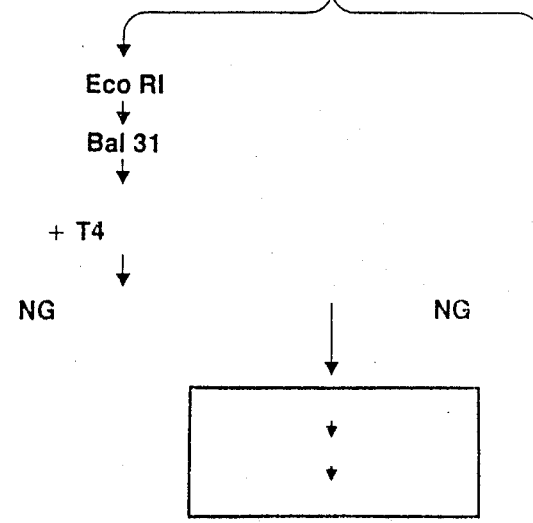

Phase DNA from five plaques positive in the enzyme immuno test is prepared, as previously described. Cleavage of the five different DNAs with Eco RI showed, besides differing bands, a common DNA band in all five phage DNAs of 5.8 Kb. The 5.8 Kb sized fragment is characterised with various restriction nucleases (FIG. 1).

A 2.2 Kb fragment is cleaved from about 5 μg. of this Eco RI fragment with the use of Pvu II. The resultant DNA fragments are separated according to their size in a low melting agarose gel and the 2.2 Kb Eco RI - Pvu II fragment is isolated. DNA fragments are isolated from low melting agarose gels by cutting out appropriate bands which are transferred to a test tube (Eppendorf tube) and mixed with about twice the volume of water. Subsequently, incubation is carried out at 65° C. for 5 to 10 minutes to melt the agarose, the sample is briefly shaken and then vigorously shaken with a half volume of phenol (neutralised with 10 mM TRIS-HCl (pH 7.5) and 1 mM EDTA, TE). The phases are separated by centrifuging for 10 minutes at 15,000 g and the upper aqueous phase is again shaken to with phenol. After centrifuging for 10 minutes at 15,000 g, the upper phase is shaken out twice with, in each case, 1 ml. of diethyl ether, the ether is evaporated at 65° C. and the DNA is precipitated with 1/10 volume of 3M sodium acetate (pH 7.2) and 2.5 fold volume of ethanol at −20° C. The DNA is sedimented by centrifuging for 10 minutes at 15,000 g, dried in a vacuum and taken up in 10 μl. TE. All further described fragment isolations take place according to this procedure.

About 4 μg. pBR 322 DNA are split with Eco RI and Pvu II and a 2.4 Kb fragment is isolated. 0.2 μg. of this pBR 322 fragment are incubated overnight, with the use of five units of T4 DNA ligase, with 0.5 μg. of the 2.2 Kb Eco RI-Pvu II fragment from the previously described λ phages. The resulting plasmid bears the designation pBT 3-2 and codes in *Escherichia coli* a biologically active creatinase.

EXAMPLE 2.

The creatinase-coding DNA from plasmid pBT 3-2 is treated exactly according to the method of Talmadge and Gilbert (Gene, 12, 235–241/1980), during the amplification phase, with nitrosoguanidine. Subsequently, the plasmid DNA, after lysis of the cells, is isolated by the CsCl-ethidium bromide method (Maniatis et al., Molecular Cloning, Cold Spring Harbor, 1982, 250–251) and plated to on to whole medium plates (LB) which contain 20 μg./ml. ampicillin. After incubation overnight at 37° C., the colonies are stamped on to LB plates upon which has previously been laid a nitrocellose filter paper (Schleicher and Schüll BA 85). After incubation of the plates for 12 to 18 hours at 37° C., the nitrocellulose filter with the colonies is lifted off and transferred into a glass petri dish of 20 cm. diameter into which 1 ml. chloroform/toluene (1:1 v/v) has been placed. Incubation takes place for 20 minutes at 37° C. The nitrocellulose filter is subsequently so placed on on indicator agarose plate that a direct contact results between the cells and the indicator plate. The colour reaction takes place in dependence upon the time and the amount of the creatinase synthesised in the individual clones. From the above-described activity screening, there is isolated the clone ED with the plasmid pBT 2a-1, DSM 3143. This plasmid codes a creatinase which accounts for about 50% of the soluble protein of the cells. FIG. 1 shows this process schematically.

Alternatively to the here-described direct NG mutagenesis, an expression increase of the creatinase can also be obtained by introduction of a foreign promotor, for example of the lactose promotor (this can be isolated as DNA fragment, for example from commercially available plasmids, such as the pUC plastids). For this purpose, plasmid pBT 3-2 is opened at the Eco RI point, so treated with the exonuclease Bal 31 that about 10 to 100 Bp are removed from each side. The lactose promotor is then ligated into the shortened plasmid pBT 3-2 with the help of the enzyme T4 ligase, with connection of the ends. This DNA is then, as described above, mutagenised with nitrosoguanidine, subsequently used for the transformation of the strain ED and the clones are tested in the described plate screening for high gene expression.

The above-mentioned indicator agarose plate represents a test system for an activity screening, the principle of which consists in that from creatine, by means of the enzymes creatinamidinohydrolase and sarcosine oxidase, the hydrogen peroxide formed is split by means of peroxidase (POD) into ½ $O_2$ and water and the oxygen is allowed to react with a colour indicator system, for example of 4-aminoantipyrine (4-AAP) and the potassium salt of N-ethyl-N-(sulphoethyl)-3-methylaniline (EST). A blue-violet coloration results which, in the case of excess of the enzymes sarcosine oxidase and peroxidase, represents a measure for the creatinamidinohydrolase synthesised in the colonies.

Test principle:

creatine + $H_2O$ $\xrightarrow{\text{creatinamidinohydrolase}}$ sarcosine + urea sarcosine + $O_2$ + $H_2O$ $\xrightarrow{\text{sarcosine oxidase}}$

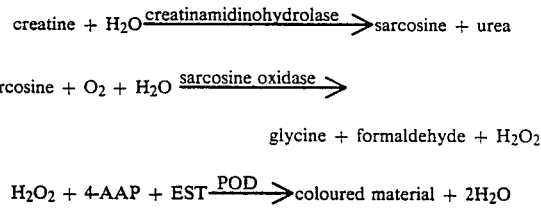

glycine + formaldehyde + $H_2O_2$ $H_2O_2$ + 4-AAP + EST $\xrightarrow{\text{POD}}$ coloured material + $2H_2O$

| Composition of the creatinamidinohydrolase activity screening system | |
|---|---|
| 1. creatine | 10 mM end concentration |
| 2. sodium azide | 0.5 mM end concentration |
| 3. tris-HCl (pH 7.8) | 20 mM end concentration |
| 4. sarcosine oxidase | 5 U/ml. end concentration |
| 5. peroxidase | 2.5 U/ml end concentration |
| 6. 4-AAP | 0.25 mg./ml. end concentration |
| 7. EST | 1.5 mg./ml. end concentration |

The reagents stated above under 1 to 7 are dissolved and mixed with the same volume of low melting agarose (2%) and 6 ml. are poured into a Petri dish. The plates can be stored about 2 weeks at 4° C. in darkness.

EXAMPLE 3.

Figure 2:
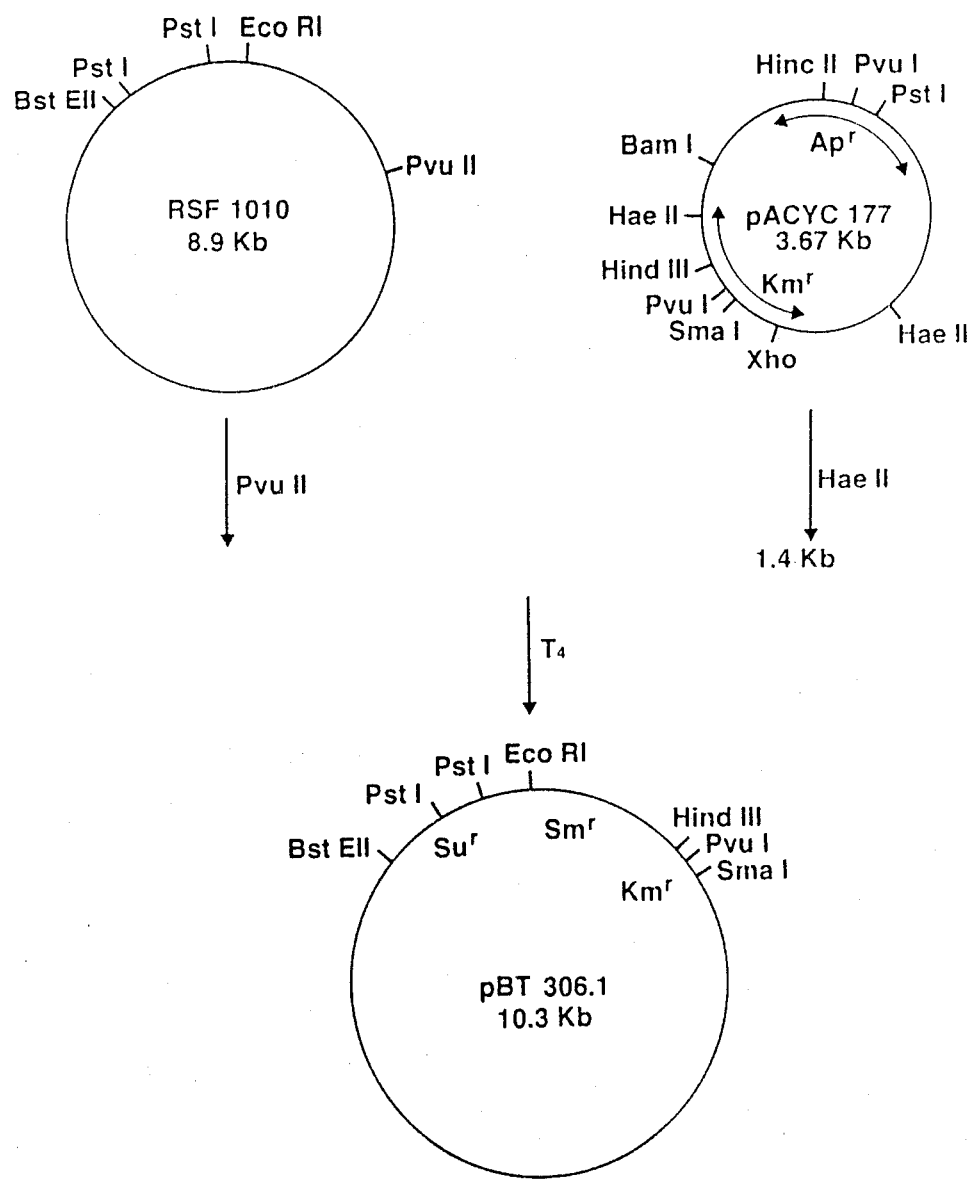
FIG. 2 shows the production, according to the present invention, of the plasmid pBT 306.1 from the plasmids RSF 1010 and pACYC 177.

For the cloning and expression of the cloned creatinamidinohydrolase into *Pseudomonas putida*, plasmid RSF 1010 (Bagdasarian et al., Gene 16, 237–247/1981) is used. RSF 1010 is linearised with Pvu II and from plasmid pACYC 177 (Chang and Cohen, J. Bacteriol., 134, 1143–1156/1978), after Hae II splitting, the 1.4 Kb fragment is isolated. 0.2 μg. RSF 1010 DNA are linked with 1 μg. of the Hae II fragment, with the use of T4 ligase, the resulting plasmid being pBT 306.1 (FIG. 2). RSF 1010 and derivatives of this plasmid are characterised by a wide host range (Gene, 16, 237–247/1981) and can be used, for example, for amplification not only in Pseudomonas but also in *Escherichia coli*. Plasmid pBT 2a-1 is split with PVU I and PVU Ii and the 2.8 Kb fragment is isolated and pBT 306.1 is split with Pvu I and Sma I and the 10 Kb fragment isolated. 0.5 μg. of the vector DNA is ligated with 0.5 μg. of the Pvu I - Pvu II fragment. *Escherichia coli* ED is transformed and creatinasecoding clones are identified with the help of the previously described plate activity screening test. DNA is prepared from one of the positive clones according to the previously described CsCl-ethidium bromide method. The plasmid bears the designation pBT 306.16, DSM 3149P (FIG. 3).

The transformation of plasmid DNA into *Pseudomonas putida* 2440 takes place exactly according to the method of Franklin et al. in: Microbiol. Degradation of Xenobiotics and Recalcitrant Compounds, Leisinger, Cook, Hütter and Nuesch, eds., 1981, pp. 109–130. Positive clones are identified with the help of the plate activity screening test. This is possible in the case of *Pseudomonas putida* 2440, although this strain contains a chomosomal coded creatinamidinohydrolase, since the expression of the plasmid-coded creatinamidinohydrolase takes place constitutively. This differing feature permits the discrimination between chromosomal-coded and plasmid-coded creatinamidinohydrolase.

EXAMPLE 4.

The determination of the creatinamidinohydrolase activity takes place by way of the detection of the ammonium ions formed by the reaction sequence with urease with the test combination "urea" (Boehringer Mannheim, Order No.124770).

For the determination of the creatinamidinohydrolase, the wild type *Pseudomonas putida* 2440 is incubated overnight at 30° C. in LB medium (5 ml.) which contains 1% creatine. The cells are harvested by centrifuging and washed once in 50 mM phosphate buffer pH 7.5. The cells are taken up in the original volume in phosphate buffer (50 mM, pH 7.5) and digested by ultrasonic treatment (50 mM, pH 7.5) and digested by ultrasonic treatment (4 x 30 seconds). Culturing and digestion of cells which contains a creatinamidinohydrolase-coding plasmid takes place in the same way a described above, with the exception that the medium contains no creatine for induction and that it is selectioned on the plasmid by the addition of ampicillin (20 µg./ml. for plasmid pBT 3-2, pBT 2a-1) or streptomycin (200 µg./ml. for plasmid pBT 306.16). The growth of the cultures takes place for *Pseudomonas putida* at 30° C. and for *Escherichia coli* at 37° C.

| | Creatinamidinohydrolase in *Pseudomonas putida* and *Escherichia coli* | | |
|---|---|---|---|
| | strain/plasmid | activity U/l. | culture |
| (1) | *Pseudomonas putida* 2440 | 1 | − creatine |
| (2) | " | 250 | + creatine |
| (3) | *Pseudomonas putida* 2440/ pBT 306.16 | 1800 | − creatine |
| (4) | *Escherichia coli* ED | — | ± creatine |
| (5) | *Escherichia coli* ED/ pBT 3-2 | 30 | − creatine |
| (6) | *Escherichia coli* ED/ pBT 2a-1 | 2800 | − creatine |

The data show that by the cloning of the creatinamidinohydrolase (1) *Escherichia coli* bacteria obtain the new property of synthesising creatinamidinohydrolase and (2) the expression, in contradistinction to the starting strain of *Pseudomonas putida*, takes place constitutively not only for *Escherichia coli* as also for *Pseudomonas putida*. Furthermore, it can be seen that by mutagenesis of the creatinamidinohydrolase DNA, an especially high expression can be achieved. (Increasing of the litre activity in comparison with the non-induced starting strain: in the case of Pseudomonas by a factor of 1800 and in the case of *Escherichia coli* by a factor of 2800).

In *Escherichia coli* ED/pBT 2a-1 DSM 3143, the activity is 500 units/g. biomass (moist) and the specific activity is 4.5 U/mg. protein. Since the specific activity of the highly purified protein is 9 U/mg., this means that the creatinamidinohydrolase in *Escherichia coli* amounts to 50% of the soluble protein. Analysis of the crude extract in SDS gel (Laemmli, Nature, 227, 680–685/1970) shows that the creatinamidinohydrolase represents the main bands of the soluble protein fraction (FIG. 4, column 2).

EXAMPLE 5.

For cultivating in a fermenter, there are used three different *Escherichia coli* host systems, namely, *Escherichia coli* W 3350, *Escherichia coli* ED 8654 and *Escherichia coli* CSH 1. The plasmid pBT 2a-1 is transformed into the corresponding competent cells. After purification for individual colonies, a pre-culture is cultured overnight at 37° C. in DYT medium (Miller, Experiments in Molecular Genetics, Cold Spring Harbor, 1972, 433) which contains 20 µg./ml. ampicillin. The fermentation medium (DYT) is inoculated with the preculture (inoculum 1%) and, without selection for plasmid content, allowed to grow for 20 to 30 hours at 37° C. After 25 hours, the creatinamidinohydrolase activity is about 600 U/g. moist mass or 4.5 U/g. of protein.

For the fermentation of *Pseudomonas putida*, the plasmid pBT 30616 is transformed into competent cells of strain 2440 as previously described, *Pseudomonas putida* DSM 3147 being obtained.

After purification of individual colonies, a preculture is incubated overnight at 30° C. in DYT medium which contains 200 ug./ml. streptomycin. The fermentation medium (DYT) is inoculated (inoculum 1%) and the culture allowed to grow for 20 to 30 hours at 30° C. The activity after 25 hours is about 220 U/g. of moist mass or 1.8 U/mg. protein.

It will be understood that the specification and examples are illustrative but not limitative of the present invention and that other embodiments within the spirit and scope of the invention will suggest themselves to those skilled in the art.

We claim:

1. Substantially pure microorganism which constitutively produces creatinamidinohydrolase comprising a microorganism of the species *Escherichia coli* or *Pseudomonas putida* transformed by a recombinant plasmid containing DNA which constitutively expresses creatinamidinohydrolase.

2. Micro-organism of the species *Escherichia coli* according to claim 1, wherein it contains the plasmid pBT 2a-1, DSM 3148P.

3. Micro-organism of the species *Escherichia coli* or *Pseudomonas putida* according to claim 1, wherein it contains the plasmid pBT 306.16, DSM 3149P.

4. Substantially pure DNA which constitutively expresses creatinamidinohydrolase comprising nucleotide base sequence:

Met Gln Met Pro Lys Thr Leu Arg Ile Arg Asn Gly Asp Lys Val Arg Ser Thr Phe Ser
ATGCAAATGCCCAAGACGCTCCGCATCCGTAACGGCGACAAGGTTCGCTCCACCTTCTCC

Ala Gln Glu Tyr Ala Asn Arg Gln Ala Arg Leu Arg Ala His Leu Ala Ala Glu Asn Ile
GCCCAGGAATACGCCAATCGCCAAGCCAGGCTGCGCGCCCACCTGGCGGCGGAGAACATC

Asp Ala Ala Ile Phe Zhr Ser Tyr His Asn Ile Asn Tyr Tyr Ser Asp Phe Leu Tyr Cys
GACGCCGCGATCTTCACCTCGTACCACAACATCAACTACTACTCCGACTTCCTCTACTGC

Ser Phe Gly Arg Pro Tyr Ala Leu Val Val Thr His Asp Asp Val Ile Ser Ile Ser Ala
TCCTTCGGCCGCCCCTACGCGTTGGTGGTGACCCACGACGACGTCATCAGCATCAGCGCC

-continued

```
Asn Ile Asp Gly Gly Gln Pro Trp Arg Arg Thr Val Gly Thr Asp Asn Ile  Val Tyr Thr
AACATCGACGGCGGCCAGCCGTGGCGCCGCACCGTCGGCACCGACAACATCGTCTACACC

Asp Trp Gln Arg Asp Asn Tyr Phe Ala Ala Ile  Gln Gln Ala Leu Pro Lys Ala Arg Arg
GACTGGCAGCGCGATAACTACTTCGCCGCCATCCAGCAGGCGTTGCCGAAGGCCCGCCGC

Ile Gly Ile  Glu His Asp His Leu Asn Leu Gln Asn Arg Asp Lys Leu Ala Ala Arg Tyr
ATCGGCATCGAACATGACCACCTGAACCTGCAGAACCGCGACAAGCTGGCCGCGCGCTAT

Pro Asp Ala Glu Leu Val Asp Val Ala Ala Ala Cys Met Arg Met Arg Met Ile  Lys Ser
CCGGACGCCGAGCTGGTGGACGTGGCCGCCGCCTGCATGCGTATGCGCATGATCAAATCC

Ala Glu Glu His Val Met Ile  Arg His Gly Ala Arg Ile  Ala Asp Ile  Gly Gly Ala Ala
GCCGAAGAGCACGTGATGATCCGCCACGGCGCGCGCATCGCCGACATCGGTGGTGCGGCG

Val Val Glu Ala Leu Gly Asp Gln Val Pro Glu Tyr Glu Val Ala Leu His Ala Thr Gln
GTGGTCGAAGCCCTGGGCGACCAGGTACCGGAATACGAAGTGGCGCTGCATGCCACCCAG

Ala Met Val Arg Ala Ile  Ala Asp Thr Phe Glu Asp Val Glu Leu Met Asp Thr Trp Thr
GCCATGGTCCGCGCCATTGCCGATACCTTCGAGGACGTGGAGCTGATGGATACCTGGACC

Trp Phe Gln Ser Gly Ile  Asn Thr Asp Gly Ala His Asn Pro Val Thr Thr Arg Lys Val
TGGTTCCAGTCCGGCATCAACACCGACGGCGCGCACAACCCGGTGACCACCCGCAAGGTG

Asn Lys Gly Asp Ile  Leu Ser Leu Asn Cys Phe Pro Met Ile  Ala Gly Tyr Tyr Thr Ala
AACAAGGGCGACATCCTCAGCCTCAACTGCTTCCCGATGATCGCCGGCTACTACACCGCG

Leu Glu Arg Thr Leu Phe Leu Asp His Cys Ser Asp Asp His Leu Arg Leu Trp Gln Val
TTGGAGCGCACCCTGTTCCTCGACCACTGCTCGGACGACCACCTGCGTCTGTGGCAGGTC

Asn Val Glu Val His Glu Ala Gly Leu Lys Leu Ile  Lys Pro Gly Ala Arg Cys Ser Asp
AACGTCGAGGTGCATGAAGCCGGCCTGAAGCTGATCAAGCCCGGTGCGCGTTGC AGCGAT

Ile Ala Arg Glu Leu Asn Glu Ile  Phe Leu Lys His Asp Val Leu Gln Tyr Arg Thr Phe
ATCGCCCGCGAGCTGAACGAGATCTTCCTCAAGCACGACGTGCTGCAGTACCGCACCTTC

Gly Tyr Gly His Ser Phe Gly Thr Leu Ser His Tyr Tyr Gly Arg Glu Ala Gly Leu Glu
GGCTACGGCCACTCCTTCGGCACGCTCAGCCACTACTACGGCCGCGAGGCCGGGTTGGAA

Leu Arg Glu Asp Ile  Asp Thr Val Leu Glu Pro Gly Met Val Val Ser Met Glu Pro Met
CTGCGCGAGGACATCGACACCGTGCTGGAGCCGGGCATGGTGGTGTCGATGGAGCCGATG

Ile Met Leu Pro Glu Gly Leu Pro Gly Ala Gly Gly Tyr Arg Glu His Asp Ile  Leu Ile
ATCATGCTGCCGGAAGGCCTGCCGGGCGCCGGTGGCTATCGCGAGCACGACATCCTGATC

Val Asn Glu Asn Gly Ala Glu Asn Ile  Thr Lys Phe Pro Tyr Gly Pro Glu Lys Asn Ile
GTCAACGAGAACGGTGCCGAGAACATCACCAAGTTCCCCTACGGCCCGGAGAAAAACATC

Ile Arg Lys
ATCCGCAAATGA
```

5. Recombinant plasmid pBT 2a-1, DSM 3148P.

6. Recombinant plasmid pBT 306.16, DSM 3148P.

7. Process for the production of a microorganism which constitutively produces creatinamidinohydrolase comprising digesting *Pseudomonas putida* chromosomal DNA with one of EcoRI alone to form a 5.8 kb fragment or with EcoR1 and PvuII to form a 2.2 kb fragment ligating the fragment obtained into a vector which has been cleaved with one of Ecorl alone or EcoR1 and PvuII together, ligating said vector and transforming said ligated vector into an *Escherichia coli* or *Pseudomonas putida* strain receptive for said ligated vector, culturing said transformed strains to constitutively produce creatinamidinohydrolase and isolating clones which constitutively form creatinamidinohydrolase.

8. Process according to claim 7, wherein said vector is plasmid pBR322 said DNA is cleaved by EcoRI alone to form a 5.8 kb fragment and said strain is an *Escherichia coli* strain.

9. Process according to claim 7, wherein said vector is plasmid pBR322, said plasmid and said DNA are split with EcoR1 and PvuII to form a 2.3 kb fragment of pBR322 and a 2.2 kb fragment of *Pseudomonas putida* chromosomal DNA, ligating said fragments to form plasmid pBT 3-2, and said transformed strain is an *Escherichia coli* strain.

10. Process of claim 7, wherein said strain is an ampicillin resistant *Escherichia coli* strain.

11. Process according to claim 9, further comprising mutagenizing the plasmid pBT 3-2 transformed into said *Escherichia coli* strain by treating said strain following transformation with nitrosoquanidine, isolating said plasmid DNA from said transformed strain, transforming said isolated plasmid DNA into a second sample of *Escherichia coli* , screening said second strain of *Escher-*

*ichia coli* for increased creatinamidinohydrolase activity and recovering plasmid DNA from said second transformed sample of *Escherichia coli* having increased creatinamidinohydrolase activity.

12. Process according to claim 11, further comprising cleaving plasmid RSF 1010 with PvuII, cleaving plasmid pACYC 177 with Hae II to obtain a 1.4 kb DNA fragment, ligating said 1.4 kb DNA fragment into said cleaved RSF 1010 to form a new plasmid, cleaving said new plasmid with PvuI and SmaI to obtain a 10 kb fragment, cleaving plasmid pBT 2a-1 with PvuI and PvuII to obtain a 2.8 kb fragment and ligating said 1.4 kb fragment and said 2.8 kb fragment to give plasmid pBT 306.16.

13. Process according to claim 7, wherein said isolating comprises contacting transformed strains with an agarose plate containing dissolved creatine, sarcosine oxidase, peroxidase and a hydrogen peroxide color indicator system and selecting strains which form color upon contact with said agarose plate.

14. Process according to claim 13, wherein the hydrogen peroxide colour indicator system comprises 4-aminoantipyrine in combination with an N-ethyl-N-(sulphoethyl)-3-methylaniline salt.

15. E. coli cell line of claim 2, DSM 3144 comprising pBT 3-2.

* * * * *